United States Patent
Spano, Jr. et al.

(10) Patent No.: US 8,491,843 B2
(45) Date of Patent: Jul. 23, 2013

(54) SCENT NEBULIZER FOR AIR HANDLING SYSTEMS

(76) Inventors: William J. Spano, Jr., Ellicott City, MD (US); Michael E. Hart, Vancleave, MS (US)

(*) Notice: Subject to any disclaimer, the term of this patent is extended or adjusted under 35 U.S.C. 154(b) by 13 days.

(21) Appl. No.: 13/323,204

(22) Filed: Dec. 12, 2011

(65) Prior Publication Data

US 2012/0145255 A1    Jun. 14, 2012

Related U.S. Application Data

(60) Provisional application No. 61/421,691, filed on Dec. 10, 2010.

(51) Int. Cl.
*A61L 9/14* (2006.01)
(52) U.S. Cl.
USPC .............................. 422/124; 261/27; 261/72.1
(58) Field of Classification Search
USPC ............. 422/120, 123, 124; 239/44; 454/337; 261/19, 27, 72.1
See application file for complete search history.

(56) References Cited

U.S. PATENT DOCUMENTS

| | | | |
|---|---|---|---|
| 4,078,891 | A | 3/1978 | Madjar |
| 5,029,729 | A | 7/1991 | Madsen et al. |
| 5,186,869 | A | 2/1993 | Stumpf et al. |
| 5,549,247 | A | 8/1996 | Rossman et al. |
| 6,379,242 | B1 * | 4/2002 | Wiseman et al. ............. 454/337 |
| 7,387,265 | B2 | 6/2008 | Hess et al. |
| 2007/0187530 | A1 | 8/2007 | Byrd |

* cited by examiner

*Primary Examiner* — Sean E Conley
(74) *Attorney, Agent, or Firm* — Ober, Kaler, Grimes & Shriver; Royal W. Craig

(57) ABSTRACT

A jet nebulizer capable of producing a small particle mist for injection into any existing whole room/house/building air distribution system. The device pumps liquid scent from a bulk container through a supply line. The unit is turned on, a flow switch is closed, power is applied to a timer and a solenoid, opening the solenoid and starting the timer. Pressure in the supply line drops and closes the pressure switch which turns the pump on, forcing the liquid scent through a nebulizer nozzle into the air handling system. The pump runs according to the timer, and will continue to run until the timer shuts the solenoid valve. Once the timer shuts the solenoid off pressure builds in the supply line. The pressure opens the water pressure switch which turns the pump off.

9 Claims, 4 Drawing Sheets

SCENT NEBULIZER FOR AIR HANDLING SYSTEMS

CROSS-REFERENCE TO RELATED APPLICATIONS

The present application claims priority to U.S. provisional patent application Ser. No. 61/421,691 filed 10 Dec. 2010, which is incorporated herein by reference.

BACKGROUND OF THE INVENTION

1. Field of the Invention

The present invention relates to air fresheners and, more particularly, to a scent nebulizer that installs into an existing air handling system to uniquely distribute scent throughout a conditioned airspace.

2. Description of the Background

Homeowners and business proprietors alike often desire to provide a pleasant scent in their living or workplace environments. Whether for ambience or therapeutic benefit, there are myriad scents available including resins, herbs, sea scents, botanicals, and various oils. Indeed, Frankincense was a valued trade product more than 5000 years ago. There are a variety of inexpensive diffusers available capable of imparting a scent into the air by evaporation, but this method is relatively inefficient. There are other approaches. For example, heat can be used to evaporate essential oils, and it will produce a scent and fill a room. However, heat tends to alter the chemical composition of the essential oil and can destroy its odor and therapeutic value. Second, while heat does produce a nice aroma, it may not be therapeutically useful because it produces relatively large particle sizes. Large breathable molecules are filtered out by the nose hairs and nasal cavity. A particle's depth of penetration into the respiratory tract varies inversely with its size. Particles between 5 and 20 microns at best reach the upper airway: nose, larynx, trachea. Particles between 2 and 5 microns will reach the lower airways. Particles between 1 and 3 microns will reach the alveolar region deep in the lungs. Thus, methods capable of producing smaller particles are generally preferred.

Ventilation (air flow-induced evaporation) is a good way to scent smaller rooms. There is no heat involved and the chemical composition of the essential oil remains intact, but the larger size and availability of breathable molecules compromises effectiveness and therapeutic benefits.

Humidification is another way (mixing oil with water and dispersing by humidifier). Using a humidifier may produce a nice scent, but has very limited capacity since the amount of essential oil is small relative to the water.

Nebulization is absolutely the best way to provide both aroma and therapeutic healing value with essential oils. It does not alter the chemical composition of the oils. It breaks down pure essential oil molecules without separation of the mixture. It produces a particle size small enough for the lungs and body to absorb them rapidly. This is why doctors and respiratory professionals recommend the use of a nebulizer to administer scents, especially those with a medicinal or therapeutic benefit. A nebulizer is a device used to expel oils in the form of a mist inhaled into the lungs.

It is known that nebulizers can be connected to centralized and individual air moving systems to inject fluid mists. Such air moving systems may include central heat and air systems, individual air conditioners and/or heat pumps, air circulation systems, etc. Thus, nebulizers can be used in homes, commercial and industrial buildings and motor vehicles.

The general concept of a wide-area scent distribution system for incorporation in a room/building air circulation system is well-known. For example, United States Patent Application 20070187530 by Byrd, Virgil O. filed Aug. 16, 2007 shows a process for controlled injection of fluid into air movement systems for the purpose of distribution of fragrances, fluids for enhanced breathing, antibacterial fluids and other similar uses. The device is connected to an air handler system, and a programmable motor moves a scent dispersant cartridge into/out from the air flow. The cartridge wicks out the scent which is dissipated into the air. The controller is programmable to determine the times of day at which the carrier inserts the dispersant into the air passageway, and also the duration of such exposures.

U.S. Pat. No. 5,186,869 to Stumpf et al. issued Feb. 16, 1993 shows an electronically controlled central air freshening system which mounts to the side of a manifold or other air passageway, forming a part of the building air conditioning or heating system. A solid, liquid-saturated dispersant cylinder is inserted into the passageway and removed from the passageway, similar to Byrd (above). A programmable control system is can be programmed for selectable times of the day and for a set duration.

U.S. Pat. No. 5,549,247 to Rossman et al. (Leyden House Limited) issued Aug. 27, 1996 shows a scented liquid nebulizer that pumps from a bottle containing scented liquid. The liquid is nebulized by air under pressure and is dispersed through an adjustable opening in the housing.

U.S. Pat. No. 7,387,265 to Hess et al. (Microwflow Engineering SA) issued Jun. 17, 2008 shows a method and system for ambient air scenting and disinfecting that uses cartridges. The cartridges drop liquid droplets onto a piezoelectric vibrator which nebulizes it.

U.S. Pat. No. 4,078,891 to Madjar (Men-Sie Frischluftgerate-Vertriebe GmbH) issued Mar. 14, 1978 shows an air handling system comprising a sealed housing with air intake and air outlet, a blower to circulate the air, a filter, and a supply of disinfectant and/or perfume between the blower and the inlet aperture. A pre-settable timer/switch is provided to control the supply of power to the blower, for intermittently actuating said blower.

U.S. Pat. No. 5,029,729 to Madsen et al. issued Jul. 9, 1991 shows a method for dispensing perfumed vapor, to the air in a room. An electrical circuit supplies a time controlled, gradually increasing current supply to operate the dispenser so that the concentration of the vapor dispensed is kept at a constant level.

The prevalent mechanism for all nebulizers is to either use oxygen, compressed air or ultrasonic power, as means to break up liquid scent into small aerosol droplets For an a wide area air handling system it would be much more advantageous to employ a jet nebulizer that forces the liquid scent through a nebulizer nozzle into the air handling system. In addition, though the '247 patent to Rossman et al. explains how to nebulize from a bottle, the other references use scent cartridges. All employ timer/switches for intermittent actuation. None of the foregoing references provide a jet nebulizers or "atomizer" capable of pumping liquid scent from a bulk container through a supply line, and forcing the liquid scent through a nebulizer nozzle into an air handling system using a timer in combination with a pressure-deactivated pump. The specific design details of the present invention add to its utility and manufacturability, and provide significant advantages.

SUMMARY OF THE INVENTION

It is, therefore, an object of the present invention to provide a relatively simple and inexpensive jet nebulizer for whole room/house/building scent distribution via a conventional air distribution system.

It is another object to provide a jet nebulizer for pumping liquid scent from a bulk container rather than cartridges.

It is still another object to provide a jet nebulizer capable of producing a small particle mist for injection into any existing whole room/house/building air distribution system.

In accordance with the foregoing object, the present air handling system jet nebulizer is a whole room/house/building scent distribution device connectable into an air distribution system. The device pumps liquid scent from a bulk container through a supply line. The unit is turned on, a flow switch is closed, power is applied to a timer and a solenoid, opening the solenoid and starting the timer. Pressure in the supply line drops closing the pressure switch. The closing of the pressure switch turns the pump on, forcing the liquid scent through a nebulizer nozzle into the air handling system. The pump runs according to the timer, and will continue to run until the timer shuts the solenoid valve. Once the timer shuts the solenoid off pressure builds in the supply line. The pressure opens the water pressure switch which turns the pump off.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

The present invention is a jet scent nebulizer that is easily connectable to an air distribution system for pumping liquid scent from a bulk container, nebulizing it, and expelling it into an existing air distribution system.

Figure 1:
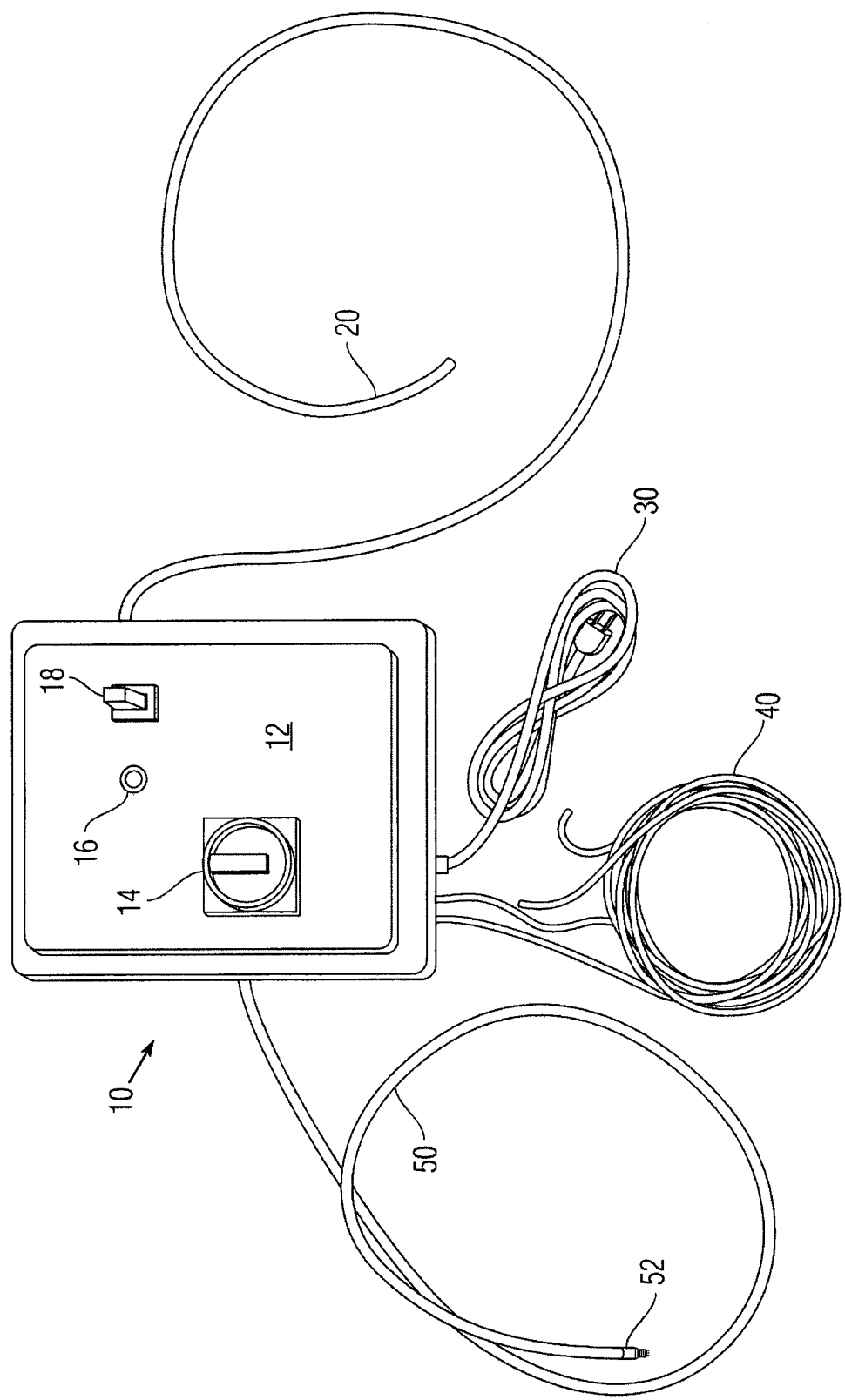
FIG. 1 is a perspective front view of a jet scent nebulizer 10 according to a preferred embodiment of the invention.

FIG. 1 is a perspective front view of the jet scent nebulizer 10 according to a preferred embodiment of the invention.

The jet scent nebulizer 10 is a scent distribution device specifically designed for connecting to an air distribution system of a whole room/house/building. The device comprises a water-resistant PVC clamshell housing 12 with front-mounted controls 14, 16, 18 and a series of peripheral cords and hoses 20, 30, 40, 50. The jet nebulizer 10 pumps liquid scent from a bulk container (not shown) in through a supply line 20, and then expels it into the existing air distribution system through output hose 50 that terminates at an atomizing nozzle 52. 120 VAC power is supplied through a power cord 30. The front controls include a manual rotary timer 4, and power ON/OFF switch 18. A nebulizer ON LED indicator 16 is visible through an aperture in the housing 12. The supply line 20 connects to an internal pump (to be described) through a first pressure switch that effectively monitors pressure in the bulk container. The first pressure switch is set to turn the pump on at 85 psi, and off at 100 psi. This ensures that the pump does not run while the bulk fluid scent container is empty. Thus, the lower pressure threshold is the "cut in" (start pumping) threshold which is 85 psi, while the upper threshold is the "cut out" (stop pumping) threshold which is 100 psi. One skilled in the art will understand that the thresholds are determined in accordance with Boyles law ($P_1 V_1 = P_2 V_2$ at constant temperature) with regard to the container size and pump characteristics and may be adjusted in accordance therewith. As described below, the present embodiment employs a commercially-available positive displacement three-chamber diaphragm pump that is equipped with an adjustable pressure switch.

When the device 10 is turned on at ON/OFF switch 18, and the manual rotary disconnect control 14 is set, this initiates a duty cycle during which the internal pump runs and scent is forced out of the output hose 50 through atomizing nozzle 52 under high pressure into an air duct of an existing air distribution system. The atomizing nozzle 52 is externally threaded to screw into a mating infeed coupling into the air distribution system, and so injects finely atomized liquid scent directly into the moving air. There are two failsafe conditions the occurrence of which will prevent the timer and/or pump from running: 1) if there is no air flow in the host air handling system, the system 10 assumes that the air handling system is off and disables itself such that the timer cannot be activated and the pump will not run; 2) if there is no fluid pressure at the pump (indicating an empty liquid scent container or other problem). The operational configuration of the device 10 implements both failsafe features in a relatively simple and inexpensive system capable of interfacing with any conventional air distribution system, yet it is highly effective at supplying an entire room/house/building with scented air. Moreover, these features allow pumping of liquid scent from a conventional bulk container, thereby eliminating the expense and hassle of replaceable cartridges.

Figure 2:
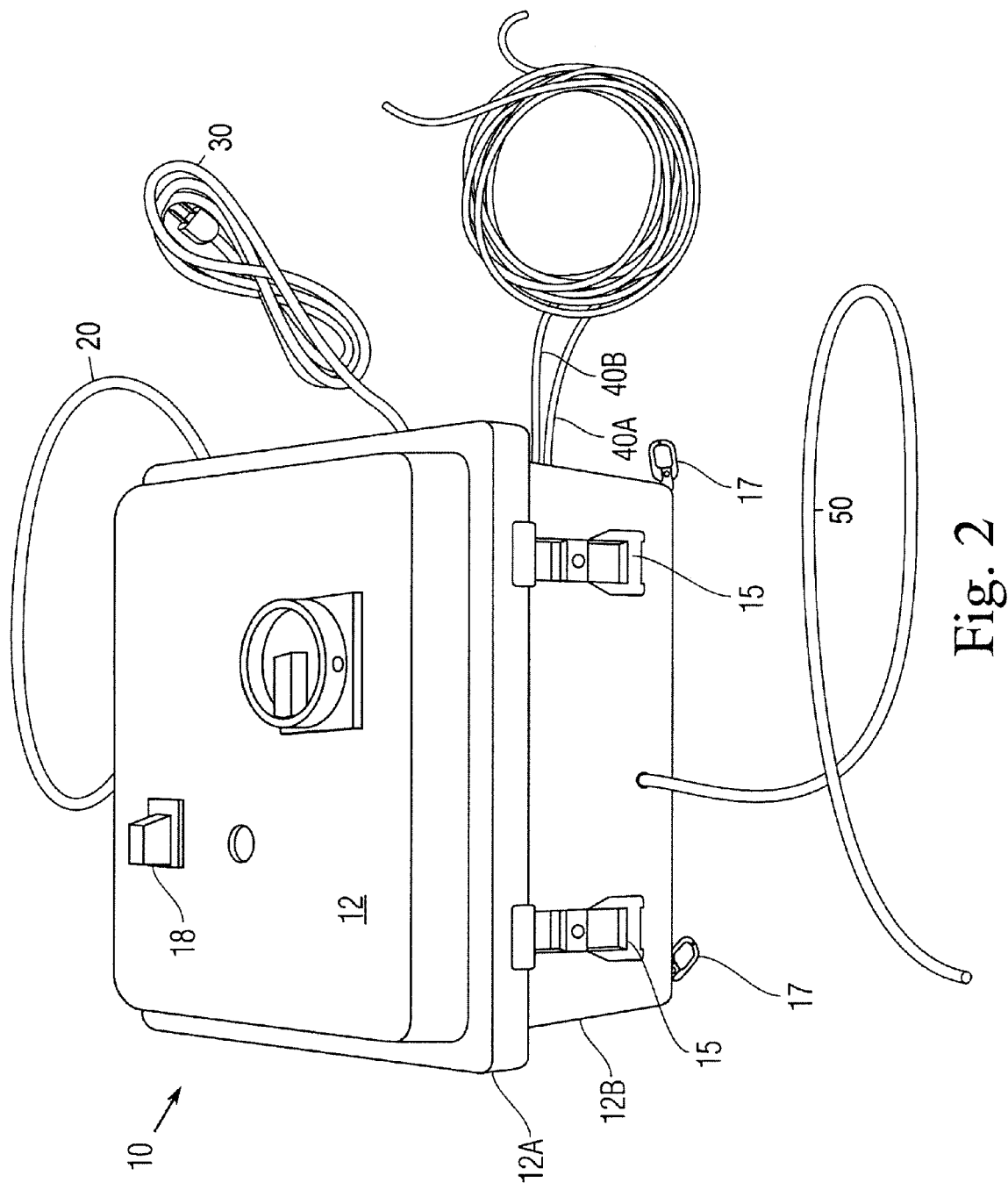
FIG. 2 is a side perspective front view of the jet scent nebulizer 10 as in FIG. 1.

FIG. 2 is a side perspective front view of the jet scent nebulizer 10 as in FIG. 1. The water-resistant PVC clamshell housing 12 further comprises a front panel 12A hingedly connected to a rectangular enclosure 12B on one side, closeable thereon, and latchable on the other side. The front panel 12A is formed with a peripheral overhang that seats atop the enclosure 12B, and the two are latched together with a pair of compression latches 15 to provide a strong compression closure. A set of four rear-corner mounting clips 17 may be provided for mounting the jet scent nebulizer 10 on a vertical wall.

Figure 3:
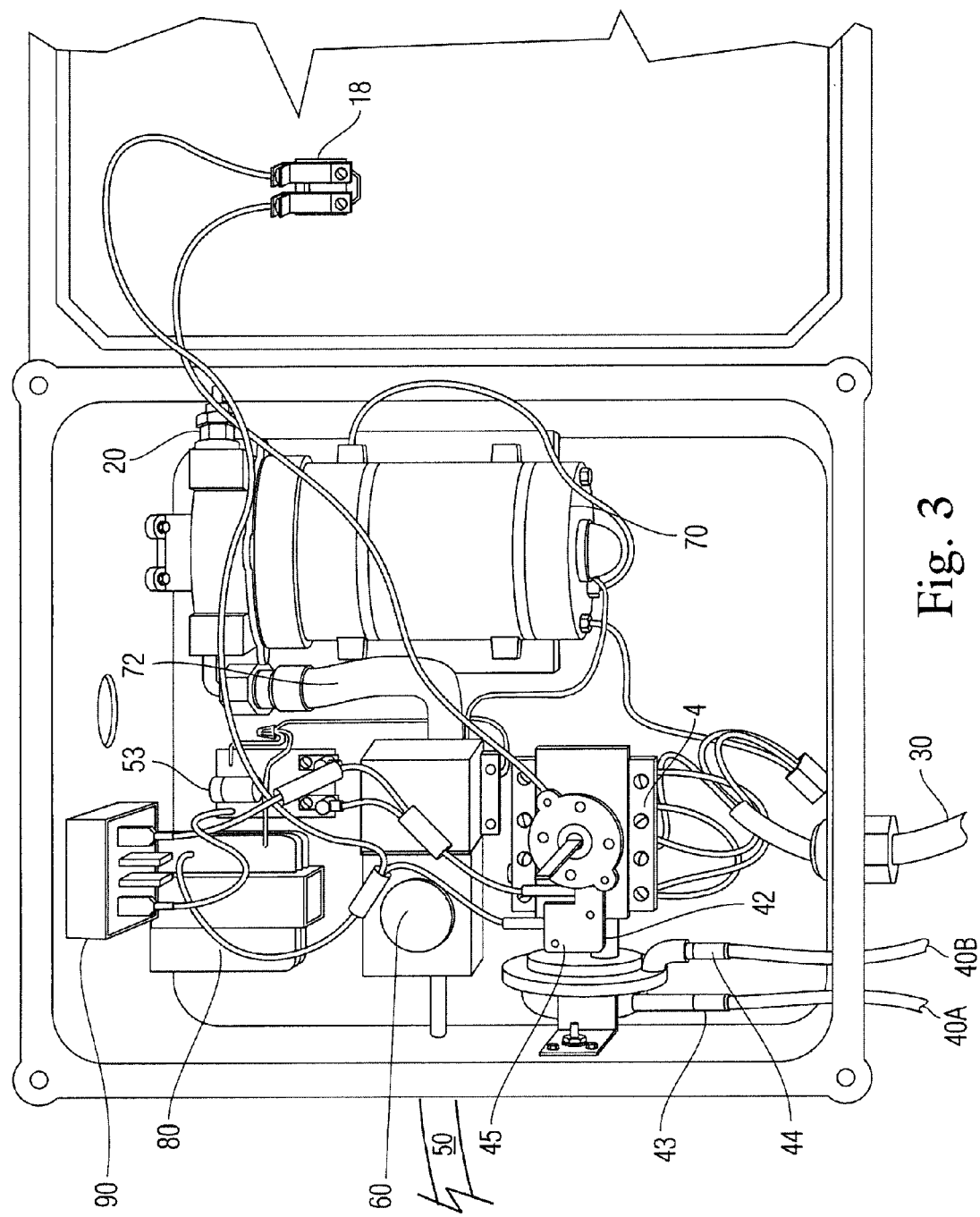
FIG. 3 is a front view of the jet scent nebulizer 10 of FIGS. 1-2 with front panel removed to reveal interior components.

FIG. 3 is a front view of the jet scent nebulizer 10 of FIGS. 1-2 with front panel 12A removed to reveal interior components.

The supply line 20 is a single ¼" hose connected through the enclosure 12B to the input port of the pump 70. As indicated, the pump 70 has an integral internal pressure switch to ensure that is only operates above a first pressure parameter and shuts of above a second higher pressure parameter.

There are also two pressure-differential tubes 40A, 40B connected across a diaphragm-type differential pressure switch 42. Tubes 40A, 40B are preferably installed upstream and downstream, respectively, in the existing air handling system ductwork and allow differential pressure sampling within the duct. By sampling upstream and downstream pressure in the existing air handling system it can be determined whether the air handling system is indeed on and moving air, in which case liquid scent can be nebulized and distributed. If not, the scent will not get very far. Consequently, the two tubes 40A, 40B are connected across a diaphragm-type differential pressure switch 42. Port 43 is connected to tube 40A, which goes into the supply duct of the of the existing air handler. When the air handler comes on, air enters tube 40B and exits tube 40A triggering a pressure drop and closing the pressure switch 42. The pressure switch 42 effectively serves as a bin monitor to determine whether the air handling system is running or not, and as pump 70 override in case it is not.

When the unit 10 is turned on and the air handling system is running, a force is exerted through the diaphragm to a pressure plate inside the switch 42. Physical deflection of the pressure plate activates micro-switch 45. When pressure recedes from the diaphragm, a light duty spring returns the pressure plate and microswitch 45 back to their original positions.

The microswitch 45 is connected to a SPST Relay with internally-mounted LED indicator light 53 that provides a visual indication of the operating state of pressure switch 42.

The manual rotary disconnect 4 sits proximate the pressure switch 42 and is a simple two-pole manually-set rotary disconnect timer for establishing a fixed length duty cycle.

A high-power positive displacement three-chamber diaphragm pump 70 occupies the right hand side of the enclosure, and upon activation pump 70 will pull liquid scent in through the input tube 20, out through a short section of internal tube 72, through a shut-off solenoid 60, and finally out through the output hose 50 through atomizing nozzle 52 under high pressure.

The pump 70 may be, for example, a Shur-Flo™ Model Number: 8000-713-238 with integral adjustable shut-off pressure switch (Range 80-100 PSI). This unit is factory set to cut out at 100 PSI, and cut on at 85 PSI.

The pump 70 liquid outlet feeds outward through a solenoid valve 60, which is a known electromechanical valve controlled by an electric current through a solenoid coil. The solenoid valve is a single-port valve in which flow is switched on or off. A wide variety of suitable solenoid valves exist and are frequently used control elements in fluidics. The present solenoid valve may be, for example, a Sporlan™ one-way normally closed solenoid valve such as model B6F1 or equivalent.

The ON/OFF switch 18 connects regulated AC power through a circuit breaker directly to the solenoid valve 60 for operation thereof. Incoming AC power from power cord 30 is stepped down at transformer 80 to a low voltage AC, which is fed through a timer 90 to the ON/OFF switch 18.

In operation, when the device 10 is turned on at ON/OFF switch 18, pressure switch 42 samples the air handling system to see if it is running If so, switch 18 both applies power to the timer 90 and opens solenoid valve 60. The user sets a duty cycle by manually setting the rotary disconnect 4. The pump 70 will run and dispense scent for so long as the timer 90 is on. The internal pressure switch in pump 70 senses pressure in the supply line 20, closes the pressure switch 42 and turns the pump on. Conversely, if the supply line 20 is not properly inserted into the bulk scent container or the container is empty, the pump 70 will not run. Once on, the pump 70 runs according to the timer 90 and will continue to run until the timer 90 times out, thereby forcing the liquid scent through the atomizer nozzle 52 at the distal end of output hose 50. When the timer 90 times out it shuts the solenoid valve 60. Once the timer 90 shuts the solenoid valve 60 off pressure builds in the internal tube 72. The pressure opens the water pressure switch in pump 70 which turns the pump 70 off.

The diaphragm-type differential pressure switch 42 serves as an override to the foregoing. One tube 43A of the differential pressure switch 42 is inserted upstream in the existing air handling system while the other tube 43B is inserted downstream. If there is no moving air in the system there is no differential pressure, the differential pressure switch 42 will remain in its normally open position, and no power will be applied to timer 90. Thus, the pump 70 cannot be activated when there is no air flow. Conversely, if there is moving air in the system there is a differential pressure, the differential pressure switch 42 will close, and power will be applied to timer 90. Thus, the pump 70 operates when there is air flow. As can be seen the operational configuration of the device 10 allows it to be relatively simple and inexpensive work with any conventional air distribution system, yet it is highly effective at supplying an entire room/house/building with scented air. Moreover, the internal tube 72 draws liquid scent from a conventional bulk container, thereby eliminating the expense and hassle of replaceable cartridges.

Figure 4:
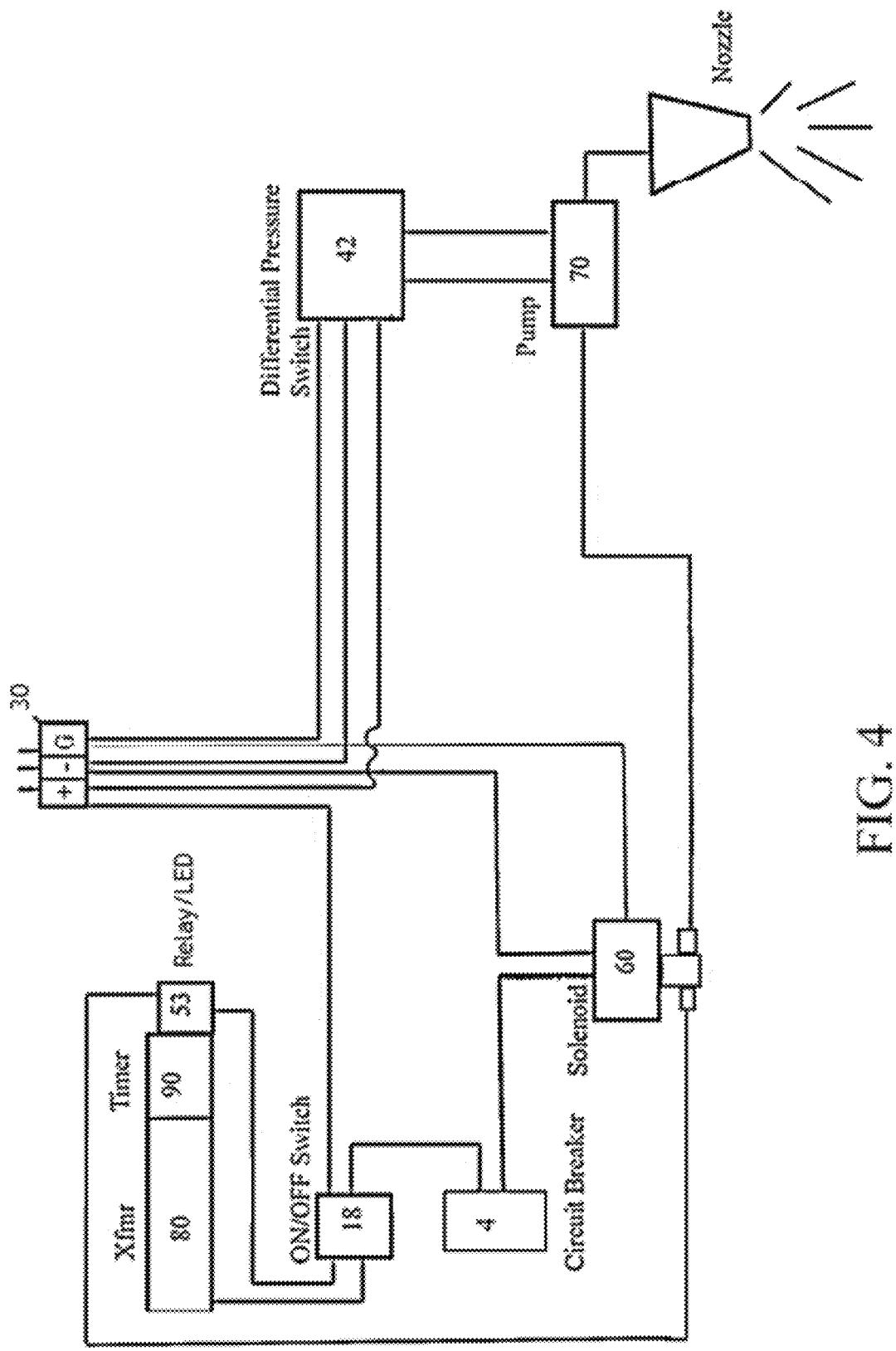
FIG. 4 is a schematic diagram of the jet scent nebulizer 10 of FIGS. 1-3.

FIG. 4 is a schematic diagram of the jet scent nebulizer 10 of FIGS. 1-3 showing both fluid and electrical connections. Generally, 120 VAC power main through transformer 80, manual rotary disconnect 4, and LED indicator 53 is connected through the ON/OFF switch 18 to timer 90. The pump 70 derives its power from the differential pressure switch 42. The pressure switch 42 has two separate ports 43, 44 for connecting the differential tubes 40A, 40B into the existing airflow handling equipment. When the airflow is moving, the pressure switch 42 closes, internally-mounted LED indicator light 53 turns on, and power is applied to the timer 90. The timer 90 may then be manually-set to establish any desired duty cycle, and upon activation will open solenoid 60. This allows fluid flow and the internal pressure switch on pump 70 will activate the pump 70, forcing liquid scent in through the input tube 20, out through a short section of internal tube 72, through the shut-off solenoid 60, and finally out through the output hose 50 through atomizing nozzle 52 under high pressure.

In view of the foregoing, it will be apparent that the above-described jet nebulizer is a simple and inexpensive approach to whole room/house/building scent distribution via any conventional air distribution system. It implements both a timed duty cycle with two safety checks (container empty and air distribution system off) without analog circuit logic, avoiding the need for more expensive microprocessor control. It allows the user to purchase bulk liquid scent containers rather than cartridges, and yet is capable of producing a small particle mist for injection across a wide area.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed:

1. A jet scent nebulizer for inducting liquid scent from a bulk container and injecting a nebulized mist of said liquid scent into an existing forced air distribution system through an air duct thereof, comprising:
   a housing;
   a timer panel mounted on said housing;
   an ON/OFF switch panel-mounted on said housing;
   a dual-port differential pressure switch mounted in said housing and having one port connected by tubing to an upstream side of said air duct, and one port connected by tubing to a downstream side of said air duct to monitor airflow through said duct;
   a pump mounted in said housing and having an inlet connected to a tube for insertion in said liquid scent bulk container, said pump having a single-port pressure switch for monitoring induction pressure in said tube;
   a fluid solenoid mounted in said housing;
   an output conduit having an atomizing jet nozzle at a distal end, said output conduit being in fluid communication with an output port of said pump through said solenoid;

whereby said pump does not run if there is no air flow in the handling system or no fluid scent in said container.

2. The jet scent nebulizer according to claim 1, wherein said single-port pressure switch activates said pump at a cut-on threshold and deactivates aid pump at a cut-out threshold.

3. The jet scent nebulizer according to claim 2, wherein said cut-on threshold is approximately 85 psi and said cut-out threshold is approximately 100 psi.

4. The jet scent nebulizer according to claim 2, wherein said dual-port differential pressure switch activates said pump when there is airflow through said duct and deactivates said pump when there is no airflow through said duct.

5. A jet scent nebulizer for inducting liquid scent from a bulk container and injecting a nebulized mist of said liquid scent into an existing forced air distribution system through an air duct thereof, comprising:
  a housing;
  a pump mounted in said housing and having an inlet connected to a tube for insertion in said liquid scent bulk container, said pump having a single-port pressure switch for monitoring induction pressure in said tube;
  a timer mounted in said housing and in electrical communication with said pump;
  a master ON/OFF switch mounted in said housing and in electrical communication with said pump;
  a differential pressure switch mounted in said housing and in electrical communication with said pump for monitoring airflow through said duct;
  an output conduit having an atomizing jet nozzle at a distal end, said output conduit being in fluid communication with an output port of said pump;
  whereby said pump does not run if there is no air flow in the handling system or no fluid scent in said container.

6. The jet scent nebulizer according to claim 5, wherein said single-port pressure switch activates said pump at a cut-on threshold and deactivates aid pump at a cut-out threshold.

7. The jet scent nebulizer according to claim 5, wherein said cut-on threshold is approximately 85 psi and said cut-out threshold is approximately 100 psi.

8. The jet scent nebulizer according to claim 5, wherein said pressure switch is a dual-port differential pressure switch.

9. The jet scent nebulizer according to claim 8, wherein said dual-port differential pressure switch activates said pump when there is airflow through said duct and deactivates said pump when there is no airflow through said duct.

* * * * *